(12) United States Patent
Itoh

(10) Patent No.: US 6,793,887 B2
(45) Date of Patent: Sep. 21, 2004

(54) SPECIMEN-INSPECTION PREPROCESSING APPARATUS

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 470 days.

(21) Appl. No.: 09/885,007

(22) Filed: Jun. 21, 2001

(65) Prior Publication Data

US 2002/0001542 A1 Jan. 3, 2002

(30) Foreign Application Priority Data

Jun. 29, 2000 (JP) ........................................ 2000-196910

(51) Int. Cl.[7] .............................. B32B 5/02; G01N 35/02
(52) U.S. Cl. .............................. 422/63; 422/64; 436/43; 436/47
(58) Field of Search ....................... 422/63, 64; 436/43, 436/47

(56) References Cited

U.S. PATENT DOCUMENTS 4,854,355 A * 8/1989 Chazot et al. .............. 141/130
4,858,767 A * 8/1989 Myers et al. ................ 209/3.1
4,880,120 A * 11/1989 Myers et al. ................ 209/3.1

FOREIGN PATENT DOCUMENTS

| JP | 1-131450 | 5/1989 |
|----|----------|--------|
| JP | 3-48766 | 5/1991 |
| JP | 4-372861 | 12/1992 |
| JP | 10-148633 | 6/1998 |
| JP | 11-316233 | 11/1999 |
| JP | 2000-88861 | 3/2000 |

* cited by examiner

Primary Examiner—Jill Warden
Assistant Examiner—La Toya I. Cross
(74) Attorney, Agent, or Firm—Nixon & Vanderhye P.C.

(57) ABSTRACT

A specimen-inspection preprocessing apparatus according to the present invention includes a desk-type housing and a plurality of specimen processing units arranged on the desk-type housing, and at least some of the plurality of specimen processing units each include a rotary conveying mechanism having a turntable.

2 Claims, 4 Drawing Sheets

SPECIMEN-INSPECTION PREPROCESSING APPARATUS

CROSS-REFERENCE TO RELATED APPLICATIONS

This application is based upon and claims the benefit of priority from the prior Japanese Patent Application No. 2000-196910, filed Jun. 29, 2000, the entire contents of which are incorporated herein by reference.

BACKGROUND OF THE INVENTION

1. Field of the Invention

The present invention relates to a specimen-inspection preprocessing apparatus for automatically preprocessing a specimen such as blood when a clinical test is conducted on the specimen.

2. Description of the Related Art

In order to run a clinical test on a specimen such as blood, the specimen should be preprocessed. Conventionally, the preprocessing has been executed manually by operators. The preprocessing for specimens required in clinic tests is considerably complicated and various steps for the preprocessing have to be taken for a long time. For this reason, the operators are likely to be infected with pathogen during the preprocessing.

To automate a specimen-inspection preprocessing operation has conventionally been considered as a method of preventing the above infection. However, facilities to automate the preprocessing operation usually become considerably large. The costs of the apparatus increase and so do the costs of facilities because a large space is required for setting the apparatus. The above prior art specimen-inspection preprocessing apparatus cannot be put to practical use for clinic tests that require that the apparatus be decreased in size, cost, and facilities cost.

BRIEF SUMMARY OF THE INVENTION

An object of the present invention is to provide a specimen-inspection preprocessing apparatus having the following advantages:

(a) A specimen-inspection preprocessing operation including a variety of complicated steps, in which an operator is very likely to be infected with pathogen, can be performed automatically.

(b) The apparatus can be formed compactly and manufactured at low costs. The setting space for the apparatus is small and the facilities costs thereof are low.

In order to attain the above object, the specimen-inspection preprocessing apparatus according to the present invention is configured as follows:

(1) A specimen-inspection preprocessing apparatus according to an aspect of the present invention comprises a desk-type housing and a plurality of specimen processing units arranged on the desk-type housing, at least some of the plurality of specimen processing units each include a rotary conveying mechanism.

(2) In the apparatus described in above (1), the rotary conveying mechanism includes a turntable having a plurality of holding sections on a peripheral portion thereof, the holding sections holding a plurality of objects to be conveyed such as specimen containers, a driving motor for turning the turntable, a turning control device for controlling the driving motor to temporarily stop the turntable when the turntable turns a predetermined angle, and carry-in/carry-out means for carrying the objects into/out of the holding sections of the turntable temporarily stopping after the turntable turns the predetermined angle, in synchronization with a control operation of the turning control device.

(3) In the apparatus described in above (1), the plurality of specimen processing units include a master-specimen carry-in unit provided on a specimen operating surface of the desk-type housing, for carrying in a master specimen contained in a master-specimen container, a usable-region detection unit for detecting a usable region of the master specimen carried in by the master-specimen carry-in unit, a stopper-removing unit for removing a stopper of the master-specimen container containing the master specimen, a slave-specimen container supply unit for supplying an empty slave-specimen container, a label issuing unit for preparing an identification label and sticking the identification label to the slave-specimen container supplied from the slave-specimen container supply unit, a pipetting tip supply unit for supplying a disposable pipetting tip, a pipetting unit on which the pipetting tip supplied from the pipetting tip supply unit is mounted and which aliquots, through the pipetting tip, the master specimen from the master-specimen container from which the stopper is removed by the stopper-removing unit and then dispenses, through the pipetting tip, a slave specimen into the slave-specimen container to which the identification label is stuck, a slave-specimen carry-out unit for carrying out the slave specimen dispensed into the slave-specimen container by the pipetting unit, and a master-specimen container carry-out unit for carrying out the master-specimen container after the aliquot operation is performed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently embodiments of the invention, and together with the general description given above and the detailed description of the embodiments given below, serve to explain the principles of the invention.

DETAILED DESCRIPTION OF THE INVENTION

Embodiment

Referring to FIGS. 1 to 6 appropriately, the structure of a specimen-inspection preprocessing apparatus according to an embodiment of the present invention will be described. In this embodiment, centrifuged blood (in which serum 1A and clot 1B are separated from each other by a separating agent 1C such as a silicon separating agent) is exemplified as a master specimen 1.

Figure 1:
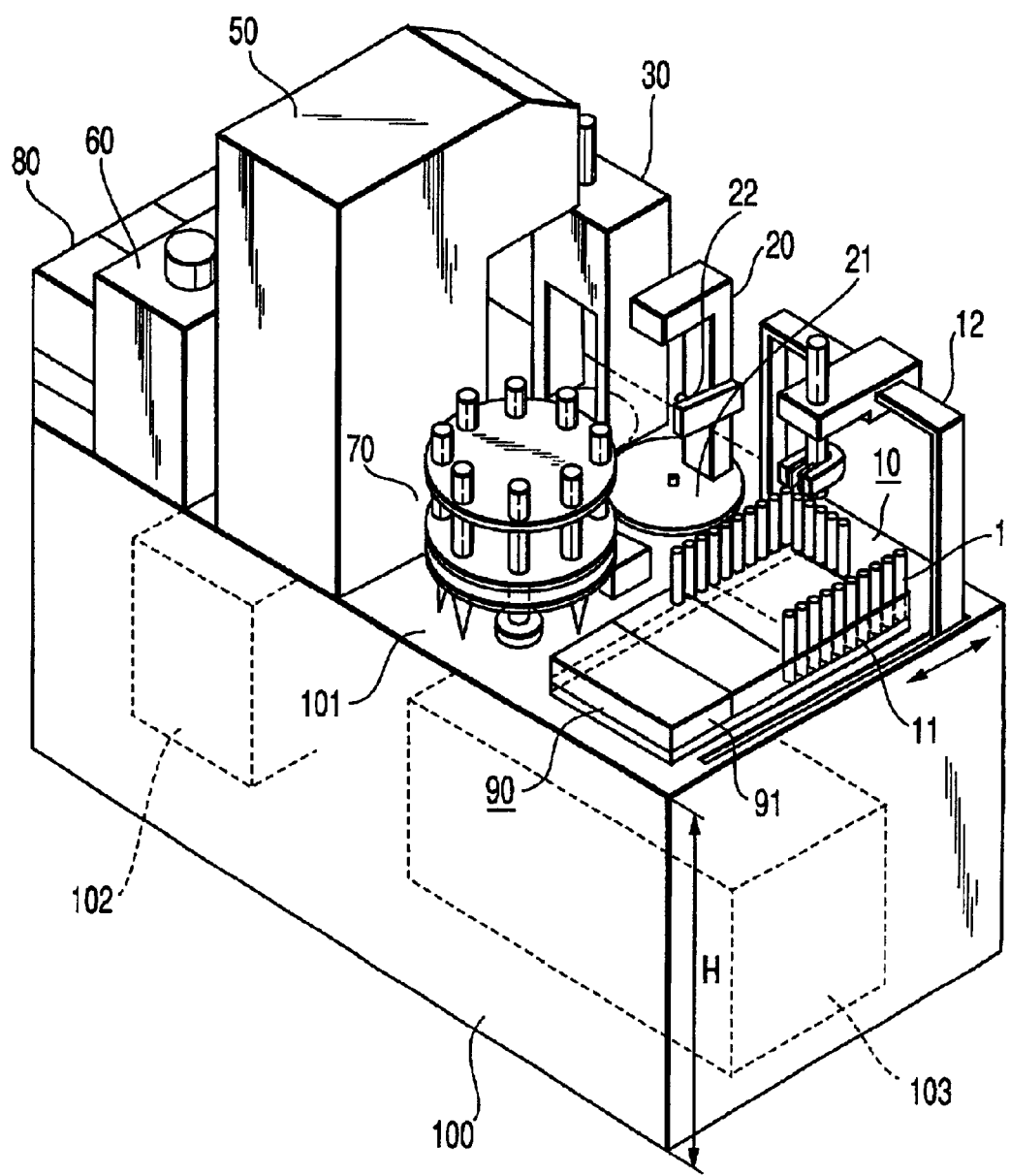
FIG. 1 is perspective view showing an outward appearance of a specimen-inspection preprocessing apparatus according to an embodiment of the present invention.
Figure 2:
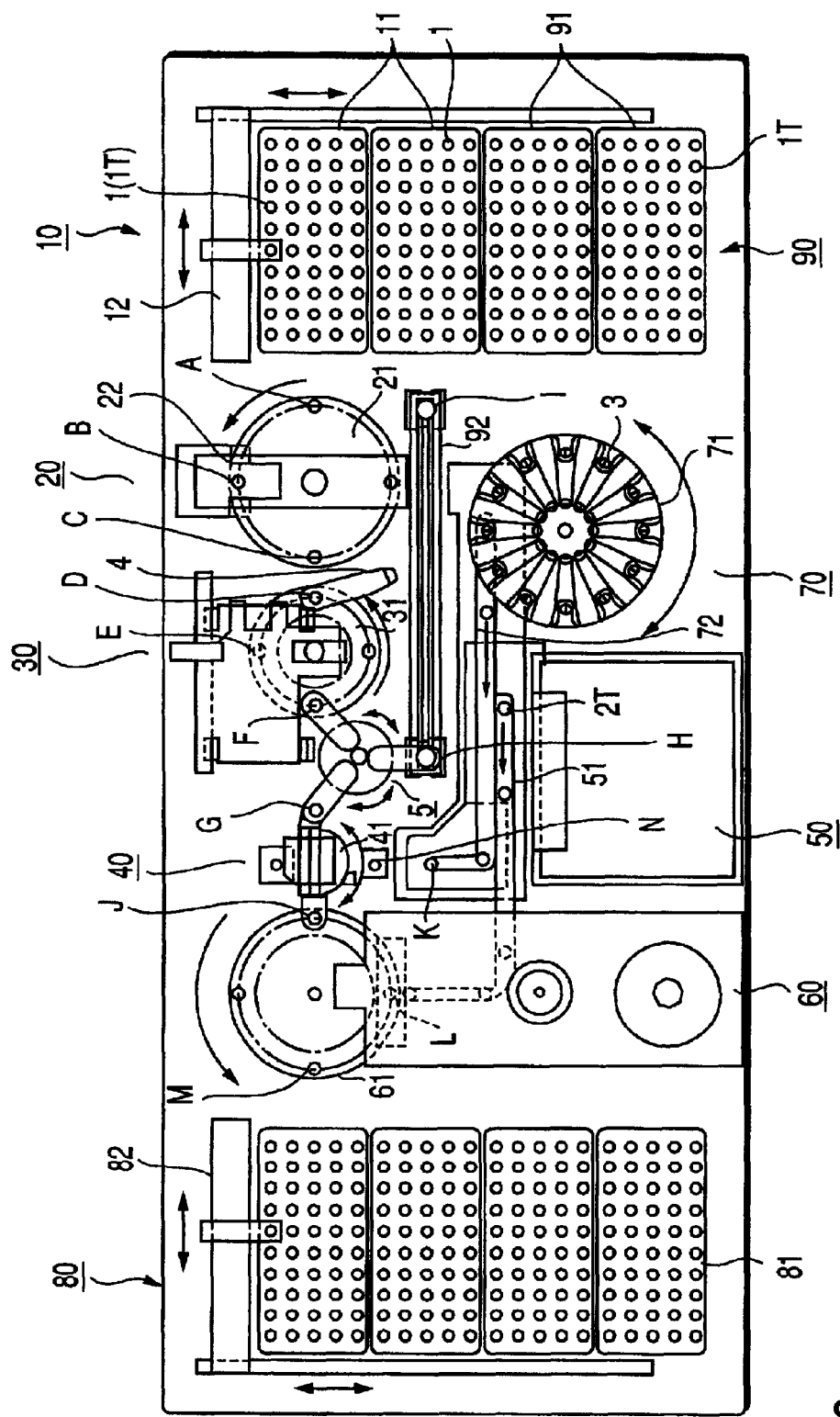
FIG. 2 is a top view of the arrangement of respective processing units of the specimen-inspection preprocessing apparatus according to the embodiment of the present invention.

As shown in FIGS. 1 and 2, a desk-type housing 100 is formed in substantially the same size as that of a large-sized desk and has a specimen operating surface 101 that is located at a given height from the ground and in parallel thereto. The housing 100 contains a controller 102 including a CPU for controlling the entire apparatus and a driving mechanism 103 including a power supply section. The controller 102 is able to receive bar code information, sort information, aliquot/dispense information and the like from a host computer (not shown) in real time. The controller 102 is also able to transmit information of pipetting of the master specimen 1 and arrangement information of a slave specimen 2 that is dispensed to the host computer in real time. On a specimen operating surface 101 of the housing 100, the following specimen processing units are arranged together with a rotary conveying mechanism in addition to a display, a keyboard, a printer, etc.

Figure 3:
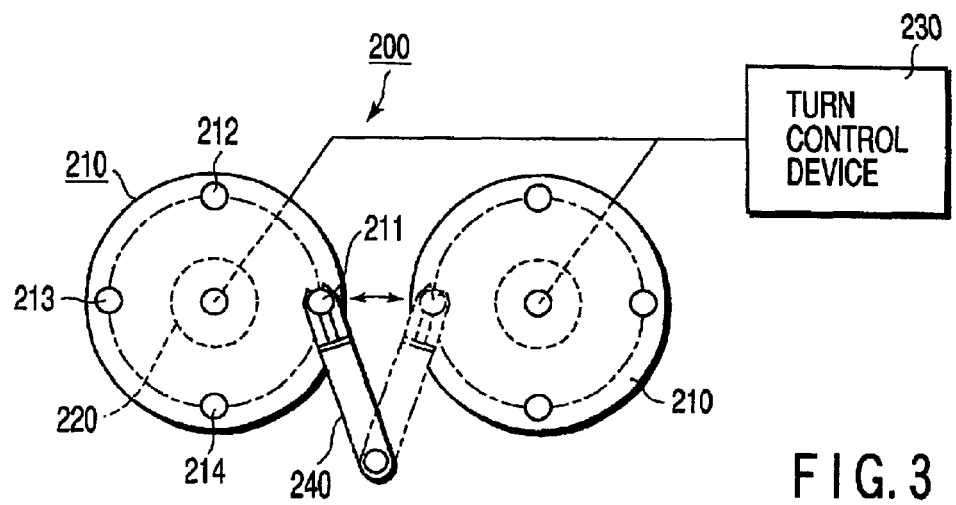
FIG. 3 is a schematic view of the structure of a rotary conveying mechanism of the specimen-inspection preprocessing apparatus according to the embodiment of the present invention.

FIG. 3 schematically shows the structure of a rotary conveying mechanism 200. In FIG. 3, reference numeral 210 indicates a turntable, 220 shows a driving motor, 230 denotes a turn control device 230, and 240 indicates a carry-in/carry-out means. The turntable 210 has on its circumference a plurality of holding sections 211 to 214 capable of holding a plurality of objects to be conveyed such as specimen containers 1 and 2. The driving motor 220 turns the turntable 210. For example, a stepping motor and a servo motor are used as the driving motor 220. The turn control device 230 controls the driving motor 220 such that the turntable 210 stops temporarily whenever it turns a predetermined angle, e.g., 90 degrees. The carry-in/carry-out means 240 includes moving arms 4 and 5 and robot arms 12 and 82, which will be described later. In synchronization with the operation of the turn control device 230, the means 240 carries an object to be conveyed out of a holding section of one turntable 210 (on the left side of FIG. 3) that turns at a given angle and stops and carries it into that of the other turntable 210 (on the right side of FIG. 3).

Let us return to FIGS. 1 and 2, the master specimens 1 are contained in master-specimen containers (test tubes) 1T and the containers 1T are set in two master-specimen carry-in racks 11 (each containing 50 test tubes).

A master-specimen carry-in unit 10 sets a master-specimen container 1T in a carry-in position A of a turntable 21 by the robot arm 12. The robot arm 12 is provided such that it can be moved in the respective directions of three axes of X, Y and Z, which intersect each other at right angles. The turntable 21 is constituted like the foregoing turntable 210 and included in a clot detecting unit 20.

Figure 4:
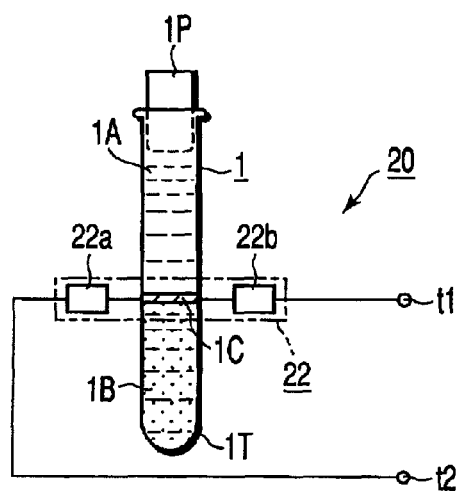
FIG. 4 is a schematic view of the structure of a clot detecting unit of the specimen-inspection preprocessing apparatus according to the embodiment of the present invention.

The clot detecting unit 20 detects a region in which the master specimen 1 can be used. The unit 20 includes a photo detector 22 constituted as illustrated in FIG. 4. The photo detector 22 detects a boundary surface between a clot 1B and a separating agent 1C of the master specimen 1, which is contained in the master specimen container 1T conveyed to a detection position B by the turntable 21. The unit 20 thus transmits the detected data to a pipetting unit 40 through terminals t1 and t2. In FIG. 4., reference numerals 22a and 22b indicate light-emitting and light-receiving elements constituting the photo detector 22, 1A shows serum, and 1P denotes a stopper for blocking the opening of the master specimen container 1T.

The container 1T of the master specimen 1, the boundary surface of which has been detected by the photo detector 22 of the unit 20, is turned and conveyed to a carry-out position C by the turntable 21. Then, the container 1T is set in a carry-in position D of a turntable 31 by means of the moving arm 4. The turntable 31 is constituted like the foregoing turntable 210 and included in a stopper removing unit 30.

The stopper removing unit 30 automatically removes the stopper 1P, which blocks the opening of the specimen container 1T turned and conveyed to a stopper-removing position E by the turntable 31, and disposes of it in a waste colleting box (not shown). Since the stopper 1P is removed and disposed of automatically, the master specimen 1 never brushes against an operator's body. Good work environment can thus be maintained. After the stopper 1P is removed, the container 1 is turned and conveyed to a carry-out position F by the turntable 31 and set in an aliquot position G of a semicircular turntable 41 by the moving arm 5. The turntable 41 is included in the pipetting unit 40. The unit 40 will be described later.

A slave-specimen container supply unit 50 stocks a number of empty slave-specimen containers (test tubes) 2T necessary for pipetting. During the pipetting, the unit 50 supplies the slave-specimen containers 2T to a label issuing unit 60 in sequence through a conveyor 51 of the unit 50. Since the slave-specimen containers 2T are automatically arranged by the slave-specimen container supply unit 50 and supplied to the label issuing unit 60, they need not always be arranged and set in the racks.

The label issuing unit 60 automatically prints a bar code label 2R, which has the same standard as that of an identification bar code label 1R stuck to the outer surface of the specimen container 1T, on the outer surface of a slave-specimen container 2T supplied from the unit 50 in a position L on a turntable 61. The turntable 61 is constituted as the turntable 210 described above and conveys the slave-specimen container 2T to which the bar code label 2R is stuck, to a position J.

Figure 5:
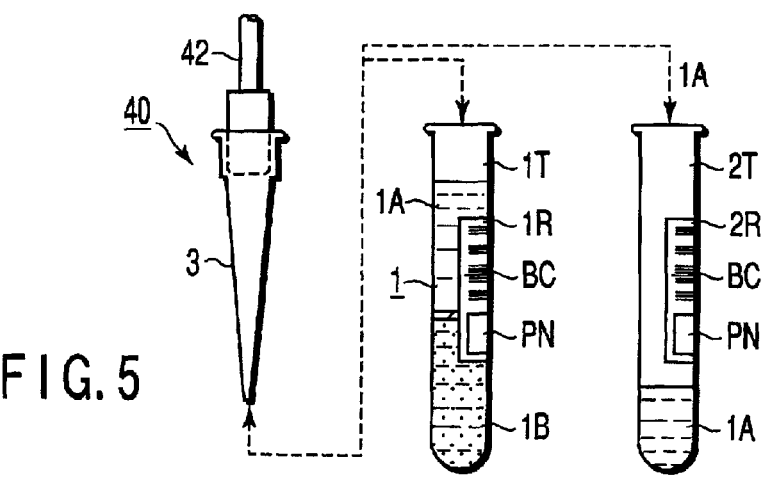
FIG. 5 is a schematic view of the structure of a pipetting unit of the specimen-inspection preprocessing apparatus according to the embodiment of the present invention.
Figure 6:
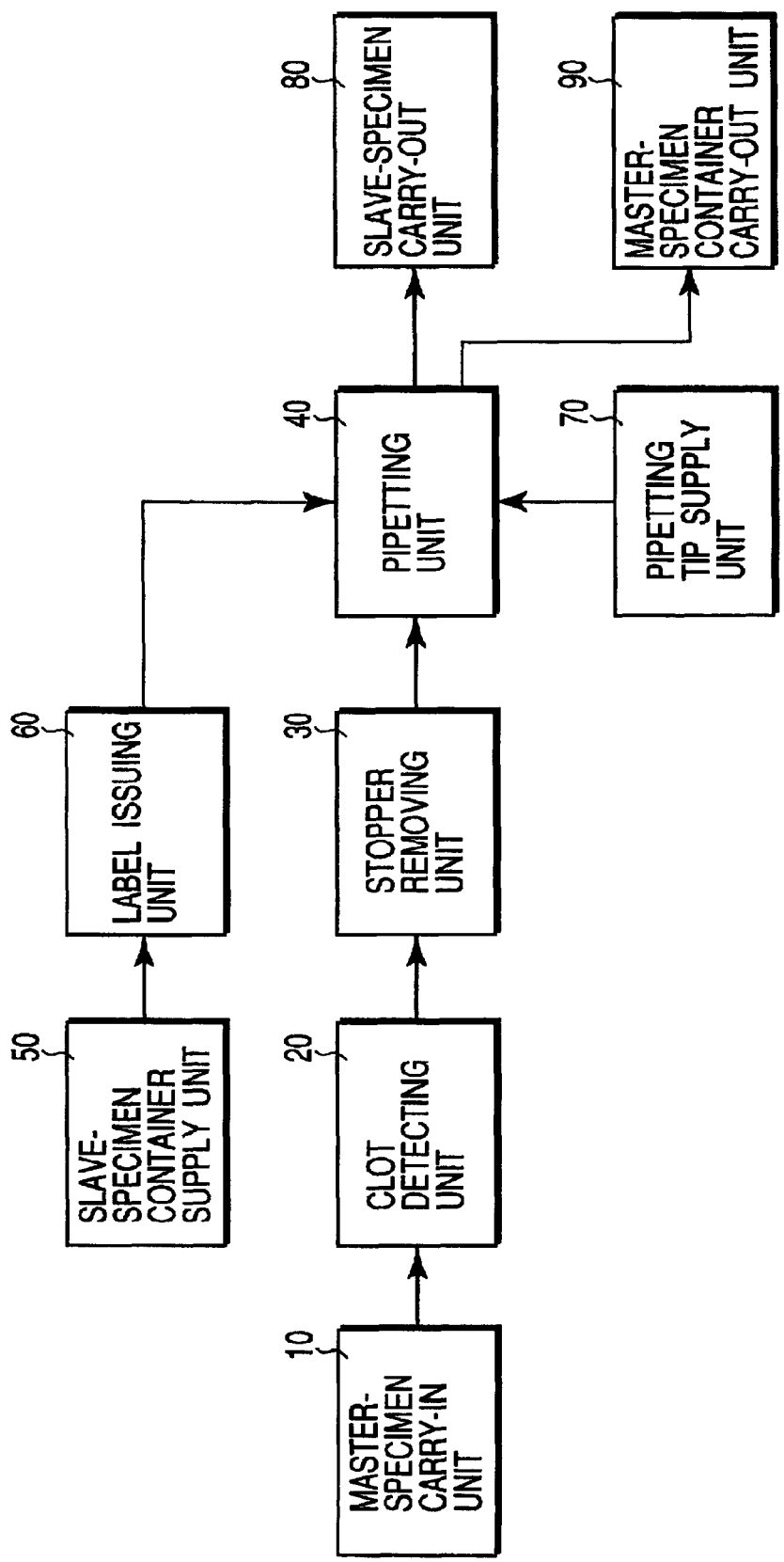
FIG. 6 is a block diagram of the structure of the specimen-inspection preprocessing apparatus according to the embodiment of the present invention.

As shown in FIG. 5, a patient's name PN as well as a bar code BC is printed on the bar code labels 1R and 2R. Consequently, an operator can discriminate specimens 1 and 2 visually and can be prevented from making a mistake such as a mix-up operation.

The label issuing unit 60 includes a bar code reader for check. When a printing error or an adhesion error occurs, the unit 60 reissues a label.

A pipetting tip supply unit 70 includes a rotary tip stocking table 71 for stocking a number of disposable pipetting tips 3 as illustrated in FIG. 5. During the pipetting, the tips 3 are automatically sent out of the table 71 and conveyed to a position K close to the pipetting unit 40 through a conveyor 72 provided adjacent to the table 71.

The pipetting unit 40 aliquots and dispense a specimen using a pneumatic aspiration nozzle 42 (see FIG. 5) attached to a peripheral portion of the turntable 41 that is turning. As the turntable 41 turns, the nozzle 42 moves to positions N, G, J, . . . and stops at each position for mounting a tip, aliquot and dispensing of a specimen, and disposal of the tip in a sequential order.

In the position N, a new pipetting tip 3 set in position K is mounted on the tip of the nozzle 42. In the aliquot position G, the serum 1A of the master specimen 1 contained in the master-specimen container 1T is absorbed into the tip 3 to perform an aliquot operation. In the dispensing position J, the aliquoted serum 1A is injected into the empty slave-specimen container 2T to which the bar code label 2R has been stuck to perform a dispense operation. The pipetting tip 3 is disposed of immediately before it moves to the position N again.

In the foregoing embodiment, the aliquot and dispense operations for specimen (serum) are carried out through the disposable pipetting tips 3. Therefore, so-called contamination between specimens is prevented.

A slave-specimen carry-out unit 80 stores the slave specimens 2, which are dispensed into the slave-specimen container 2T and moved to a position M by the turntable 61, in four slave-specimen carry-out tracks 81 (each containing 50 specimens) by means of a robot arm 82 that is constituted like the foregoing robot arm 12. The slave specimens 2 are sorted and carried out in accordance with the purpose of use. If the slave-specimen carry-out racks 81 are full, an alarm is issued.

A master-specimen container carry-out unit 90 carries out the master-specimen container 1T, which completes its aliquot operation and is turned and conveyed to a carry-out position H by the moving arm 5, to a position I close to two slave-specimen carry-out racks 91 (each containing 50 specimens) by means of a carry-out conveyor 92. The master-specimen container 1T conveyed to the position I is held in the racks 91 using the robot arm 12. The master specimen 1 of the rack 91 is carried outside the body of the apparatus. If the racks 91 are full, an alarm is issued.

The following advantages can be expected from the above embodiment:

1) A series of operations for specimens 1 and 2, such as carry-in/carry-out, issuance of labels, and pipetting, is performed automatically. Therefore, the specimens 1 and 2 are not likely to brush against an operator, which is very effective in preventing the operator from being infected with pathogen.

2) Most of the processing units arranged on the desk-type housing 100, i.e., the units 20, 30, 40, 60 and 70 include rotary conveying mechanisms using turntables 21, 32, 41, 61 and 71, respectively. Even thought the processing units are arranged close to each other, they can smoothly perform a carry-in/carry-out operation for the specimens 1 and 2 and the pipetting tips 3. It is thus possible to compactly arrange the processing units on the carry-in/carry-out surface 101 of the housing 100, whose area is very small, with the result that the apparatus can be decreased to the same size as that of a laboratory-table. Since, moreover, the structure of the rotary conveying mechanism 200 itself is very simple, the apparatus can be decreased in cost. Since, moreover, a space for setting the apparatus is small, the facilities costs can be lowered.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A specimen-inspection preprocessing apparatus comprising:

a housing; and a plurality of specimen processing units arranged on the housing, at least some of the plurality of specimen processing units each include a rotary conveying mechanism, wherein the plurality of specimen processing units include:

a master-specimen carry-in unit provided on a specimen operating surface of the housing, for carrying in a master specimen contained in a master-specimen container;

a usable-region detection unit for detecting a usable region of the master specimen carried in by the master-specimen carry-in unit;

a stopper-removing unit for removing a stopper of the master-specimen container containing the master specimen;

a slave-specimen container supply unit for supplying an empty slave-specimen container;

a label issuing unit for preparing an identification label and attaching the identification label to the slave-specimen container supplied from the slave-specimen container supply unit;

a pipetting tip supply unit for supplying a disposable pipetting tip;

a pipetting unit on which the pipetting tip supplied from the pipetting tip supply unit is mounted and which aliquots, through the pipetting tip, the master specimen from the master-specimen container from which the stopper is removed by the stopper-removing unit and then dispenses, through the pipetting tip, a slave specimen into the slave-specimen container to which the identification label is attached;

a slave-specimen carry-out unit for carrying out the slave specimen dispensed into the slave-specimen container by the pipetting unit; and a master-specimen container carry-out unit for carrying out the master-specimen container after the aliquot operation is performed.

2. The apparatus according to claim 1, wherein the rotary conveying mechanism includes:

a turntable having a plurality of holding sections on a peripheral portion thereof, the holding sections holding a plurality of objects to be conveyed;

a driving motor for turning the turntable;

a turning control device for controlling the driving motor to temporarily stop the turntable when the turntable turns a predetermined angle; and carry-in/carry-out means for carrying the objects into/out of the holding sections of the turntable temporarily stopping after the turntable turns the predetermined angle, in synchronization with a control operation of the turning control device.

* * * * *